United States Patent [19]

Greenway

[11] Patent Number: 4,630,603

[45] Date of Patent: Dec. 23, 1986

[54] WOUND DRESSING

[75] Inventor: John M. Greenway, Westwood, Mass.

[73] Assignee: The Kendall Company, Boston, Mass.

[21] Appl. No.: 829,587

[22] Filed: Feb. 13, 1986

[51] Int. Cl.[4] .............................................. A61L 15/00
[52] U.S. Cl. ................................... 128/156; 428/284; 428/286; 428/287; 428/304.4; 428/343; 428/354; 428/355; 428/356; 428/913
[58] Field of Search ............... 128/156; 428/284, 286, 428/287, 343, 354, 355, 356, 913, 304.4

[56] References Cited
U.S. PATENT DOCUMENTS 4,302,500 11/1981 Flora ................................. 428/284

4,499,139 2/1985 Schortmann ..................... 428/245

Primary Examiner—James J. Bell
Attorney, Agent, or Firm—Edward J. Scahill, Jr.

[57] ABSTRACT

A wound dressing comprising at least one ply of an aerated latex microsized hydroentangled fabric, having an adhesive disposed on at least one surface of the fabric, and a nonwoven fibrous pad material centrally mounted thereon. The present invention has sufficient hydrophobicity in the fabric to be a barrier to liquid borne bacteria while preserving comfort, air permeability, and flexibility therein. In addition to the above properties, the dressing is sterilizable, and will keep the skin beneath the dressing dry.

5 Claims, 6 Drawing Figures

WOUND DRESSING

BACKGROUND OF THE INVENTION

1. Field of Invention

This invention relates generally to wound dressings, and relates especially to an island dressing that has high air permeability, is a liquid barrier, is flexible, strong and a bacteria barrier.

2. Prior Art

Today, wound dressings consist of many different forms. One wound dressing such is that made by Johnson & Johnson under the Tradename "Bandaid", has an outer layer or backing of a porous plastic film having an adhesive and a non-woven pad material attached to the film's inner surface. When the dressing is applied to a patient the nonwoven pad is placed over a wound and comes into contact with the skin. The porous plastic film backing in the prior art is supposedly used to let moisture that is trapped under the dressing evaporate out through the pores in it. This is usually not the case, because although there are pores in the dressing, moisture trapped under the dressing against the skin does not evaporate out through them. This is quite evident in a visual observation of the skin after the dressing has been removed, because the skin is moist and wrinkled. This condition is mainly due to the fact that the pores in the plastic film permits air to circulate only in areas where the pores are located. When moisture is trapped close to the skin it causes the skin to remain moist, thereby wrinkling the skin. As long as the skin remains moist, a wound may be subjected to bacteria and a long healing time. In addition, this type of prior art dressing will trap moisture, such as perspiration against the skin. A condition that will exacerbate the wrinkling of the patient's skin.

Another prior art wound dressing is a product manufactured by Medtech Laboratories, Inc. of Cody, Wyo., made under the trademark "New Skin." This prior art is a clear spray coating, whereby a protective coating is sprayed from an aerosol can, to cover an open wound. There are many disadvantages with this prior art. Some of the disadvantages, are ones the manufacturer has printed on the product such as, "the inhalation of the chemicals used herein may be harmful;" "the chemical content must be kept away from eyes and other mucous membranes, otherwise they may be damaged." Another disadvantage is that the contents when sprayed onto a wound causes the wound to sting, adding to the discomfort of the person who uses it.

In U.S. Pat. No. 3,247,845, a dressing fabric is described that is made from silk or cotton, and is impregnated with a flexible collodion solution. The flexible collodion solution is then dried. When applying this dressing, the collodion solution must be redissolved in situ over the wound with an appropriate solvent. This type of dressing has many disadvantages. One such disadvantage is that a solvent must be used to activate the solution within the dressing, before the dressing becomes effective. Still another disadvantage is that this type of dressing requires a person to carry both a dressing and a solvent in their possession to properly use it.

The prior art has tried to achieve the aforementioned properties of air permeability, liquid resistance, flexibility, strength and bacteria resistance in their wound dressings, but has been only partially successful. The present invention has achieved these properties by using a unique fabric structure that is superior to prior art.

An object of this invention is to provide a wound dressing that can be produced economically.

Another object of this invention is to provide a wound dressing substantially more conformable and comfortable than prior art.

Still another object of this invention is to provide a wound dressing that is uniformly breathable, due to better air permeability of said dressing, while at the same time repelling liquid, and bacteria.

An additional object of this invention is to provide a wound dressing with strength and flexibility.

Still another object of this invention is to provide a wound dressing that is substantially free of lint.

Another object of this invention is to provide a wound dressing that is sterilizable.

Other objects will be apparent from the remainder of the specifications and claims.

SUMMARY OF THE INVENTION

The present invention relates to a wound dressing, comprising an aerated latex microsized hydroentangled fibrous fabric having an adhesive disposed on at least one surface of said fabric, and a nonwoven pad material centrally mounted thereon. Microsizing is defined herein as the application of a chemical to a fabric to create microsize pores, which are necessary to establish a bacterial barrier in a fabric while preserving air permeability thereof. The particular properties of this fabric allow the fabric to remain soft, air permeable, flexible and strong. The fabric structure also makes the fabric conducive to providing a bacterial barrier with hydrophobicity, thus lending itself for use as a wound dressing.

DESCRIPTION OF PREFERRED EMBODIMENT

Figure 1:
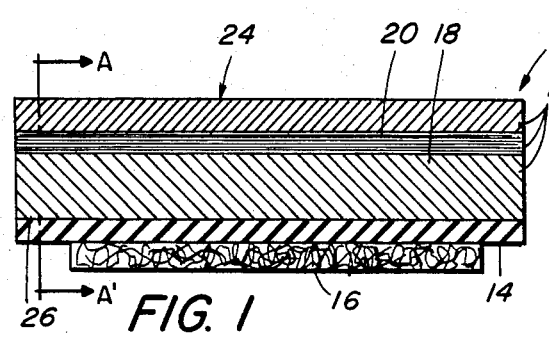
FIG. 1 illustrates a sectional view of a single ply microsized hydroentangled dressing fabric, a pressure sensitive adhesive and a nonwoven pad material.
Figure 3:
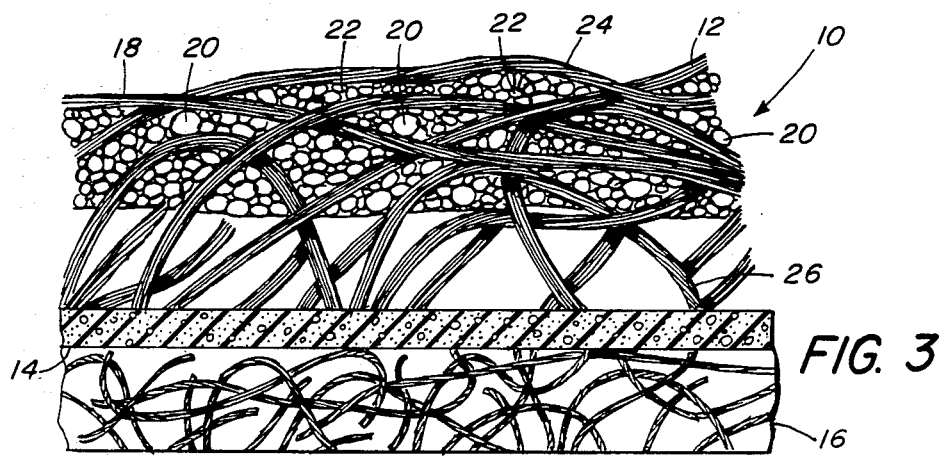
FIG. 3 illustrates the porous structure of the present embodiment, which is a further magnified view of FIG. 1.

FIG. 1 illustrates a wound dressing 10, comprising a microsized fabric 12, as described in U.S. Pat. No. 4,499,139 of common assignee, and herein incorporated by reference, an adhesive 14 disposed on at least one surface of the fabric 12, and a nonwoven pad material 16 centrally mounted to the fabric 12 by the adhesive 14. As shown in FIGS. 1 and 3 the referenced fabric 12 consists of hydroentangled textile length fibers 18 having a latex microporous froth sizing 20 within the fiber structure. Hydroentangling of nonwoven material is done by subjecting a fibrous web of textile length fibers to a series of high pressure water jets, to entangle the fibers therein. Froth sizing, as described in U.S. Pat. No. 4,499,139, is a latex mixture that is aerated by an Oakes Foamer as described in the above-referenced patent. Due to the extremely low cost of the materials used in the present invention, it is more economical to produce than prior art dressings. In addition to hydroentangled fabrics, any woven or nonwoven material may also function as a dressing material when made according to U.S. Pat. No. 4,499,139. Although the preferred embodiment is primarily for use as a wound dressing, it may be used wherever a protective covering is needed.

For purposes of this invention where we speak of bacterial barriers we mean materials constructed in such a manner so as to prevent bacteria from penetrating through them.

The present invention dressing made from the referenced microsized fabric has the look and feel of a cloth. Because the present invention fabric has the qualities of a cloth, it is conformable, comfortable, and flexible. To check for softness, conformability, or comfort of a fabric, tests are available which are discussed herein. The test for softness and conformablity is conducted according to the Industrial Nonwoven Disposable Association Standard Test, IST 90.0-75(R77). The test is a Softness Handle-O-Meter test where forces are used to bend the fabric to determine the drape, conformability, hand and softness.

In addition, to insure the fabric is comfortable, an internal test is performed, which is called a Cytotoxic Test. The Cytotoxic Test is actually a battery of tests which insures that the fibers and other components used on or within the fabric are non-irrating when placed against human skin. The present invention fabric passed these tests.

A flexibility test is performed in accordance with the Industrial Nonwoven Disposable Association Standard Test, IST30.0-70(R77), and the American Society of Testing Materials, ASTM D774-67. The test for flexibility is called the Mullen Burst Test, whereby a circular diaphragm is placed against the fabric to be tested. Pressure is then applied to the diaphragm until the fabric ruptures.

The present invention also retains substantial strength due to its hydroentangled construction. The strength tests are conducted in accordance with IST 110.0-70(R77), ASTM D1682.64 and ASTM D2261-71. The strength tests consist of a Tongue Test and a tensile strength test. The Tongue Test, tests the ability of the fabric not to tear. In this test, the fabric is cut into a rectangular piece 3 inches wide by 8 inches long. The rectangular piece of fabric is then slit in the center, half way down the fabric in the 3 inch width direction. The two ends of the slit piece are then attached to an Instron Tester (a tensile strength test machine made by Instron Corporation of Canton, Mass.) and subjected to a tearing force. This force is then recorded. The tensile strength test consists of taking a strip of fabric one inch wide by eight inches long and attaching said strip to an Instron tester. A force is exerted by the tester in the vertical direction to determine what force it takes to break or tear the fabric. When the fabric breaks, the force is then recorded.

The unique stratification of the present fabric essentially makes a two-sided fabric, as shown in FIG. 3 wherein, the outer surface fibers 24 of the fabric 12 are subjected to latex froth sizing 20 to give a protective coating, while the inner surface fibers 26 of the fabric 12 remain substantially froth free, thus pliable and soft. The inner surface fibers 26 are then coated with a porous pressure sensitive adhesive 14. The adhesive 14 on the fabric 12, as shown in FIG. 1, is applied to the inner surface fibers 26 of the fabric 12 by knife application, reverse roll application or other conventional procedures. After the adhesive 14 is applied a pad of nonwoven material 16 is assembled onto the adhesive 14, with the adhesive holding it in place.

Figure 4:
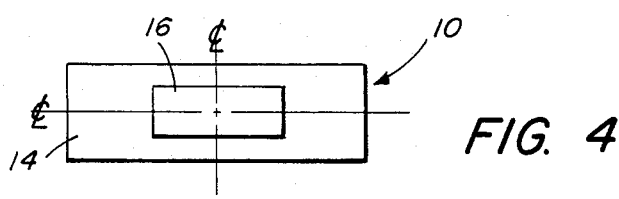
FIG. 4 is a bottom view of the present invention.

As shown in FIG. 4, the nonwoven material 16 is centrally located on the wound dressing 10. The nonwoven pad material may consist of any natural or synthetic fiber, such as cotton, polyester, rayon, acrylic, polypropylene, nylon, or polyethelene or blends thereof. The preferred nonwoven pad material is cotton. The adhesive that is applied to the microsized fabric may be any porous solvent pressure sensitive adhesive base such as a polyacrylate. Such a porous adhesive may have pore sizes that range between 10 microns and 100 microns. However, it is preferred that the pore size in the adhesive be between 25 to 40 microns. Although other types of adhesives may be used, the preferred adhesive is used because it has a structure that allows it to be extremely air permeable. This enhances the air circulation in the dressing produced thereby. Air circulation is an important property of a bandage and will be discussed in detail in subsequent paragraphs. Although the inner surface fibers are coated with an adhesive, they remain soft and pliable. This is due to the porous nature of the adhesive, and that fact that the inner surface fibers are not coated with the froth. In addition, because the fabric is hydroentangled and has a froth sizing within it, it is virtually lint free. Furthermore, because it is lint free, there are no air borne or loose fibers that would contaminate an open wound. To determine the amount of lint present in a fabric a test is conducted that consists of rubbing a number zero emery cloth against both surfaces of a fabric in a circular motion using at least 15 cycles. The number of cycles it takes to raise fibers is then recorded. No lint was detected in the present invention bandage after the test.

Referring to the drawings, FIG. 3 shows the micropores 22 of the froth 20 situated between and adjacent to the top surface fibers 24 of the fabric. Micropores may be defined as open pores ranging in size from 10 to 100 microns. As described in U.S. Pat. No. 4,499,139, of common assignee, these pores are created by dispersing air, which creates air bubbles, in a latex liquid. The frothed liquid once deposited on a fabric is then heated to solidify the latex. The heat in curing the latex bursts the air bubbles thereby creating the micropores. These micropores 22 created from the froth 20 are important for two reasons. The first is that these micropores 22 allow the free movement of air through the fabric. In other words, these micropores 22 give substantial air permeability to the fabric. An air permeability test is conducted according to the Industrial Nonwoven Disposable Association Standard Test IST 70.1-70(R77) and Federal method 5452, referred to as the Frazier Test. The Frazier Test is to pass a certain volume of air through a certain area of fabric per unit time under a low pressure differential. Thus, the greater the volume of air passed through a fabric, the higher the air permeability.

When moisture is created by a covered wound, it is essential that this moisture be allowed to escape away from the wound out through the covering. This cannot be done unless the wound dressing used has substantial air permeability. Thus, air permeability is an important property of a dressing. Air permeability permits moisture formed on the wearer's skin under a wound dressing, to evaporate, and to be carried by the circulation of air, out through the dressing. More importantly, air permeability in a dressing fabric substantially eliminates maceration of the skin. Maceration is defined for the purpose of this application as the puckering, wrinkling and whitening of the skin due to the prolonged exposure of moisture to the skin. Confinement of moisture on the skin usually results from covering the skin for a prolonged period of time with a dressing fabric. The present invention dressing does not allow maceration to take place because the dressing material is quite air permeable, thus allowing substantial evaporation to occur, and causing the skin to remain substantially dry. In addition, the dryness of the skin aids in the healing of a wound. Furthermore, the finished fabric, because of its air permeability, is highly sterilizable.

An air permeability test was performed between the present invention dressing and a prior art dressing made by Johnson and Johnson under the Tradename "Bandaid", which is one of the presently accepted wound dressings. It was found that the prior art dressing had a higher air permeability than the present invention, as measured by a Frazier Test. This is indicated in the following test results.

| Sample | Air Permeability FT3/FT2/Min. |
| --- | --- |
| Microsized wound dressing (with adhesive) | 25 |
| Prior Art wound dressing (J & J) | 102 |

Figure 5:
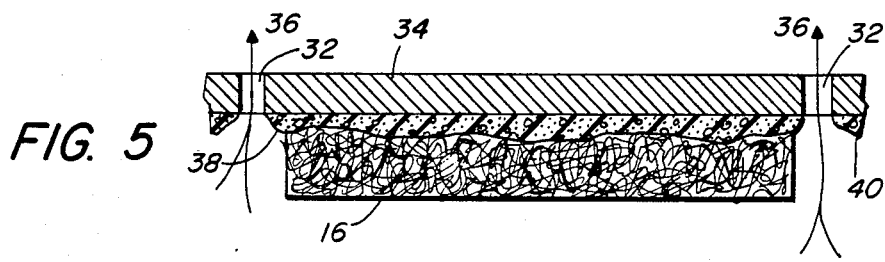
FIG. 5 is a sectional view of a prior art wound dressing and further shows the build-up of moisture thereunder.
Figure 6:
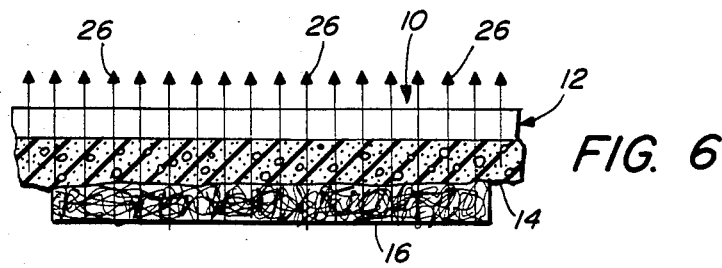
FIG. 6 further illustrates the present invention, and the permeability of the dressing, by showing moisture evaporating out through the pores in the dressing.

Although this may seem to illustrate that the prior art would function better than the present invention, it was observed that the prior art dressing macerated the skin, while the present invention dressing did not. This lack of maceration of the skin by the present invention was an unexpected result. It has been determined that because the prior art pores or perforations 32 are isolated from each other, as illustrated in FIG. 5, moisture 38 remained trapped under the adhesive 40 of the prior art dressing 34, in the areas between the pores 32, when the dressing is applied to the skin. This does not promote good air circulation 36, as illustrated in FIG. 5. Very little, if any evaporation of moisture takes place, thus maceration of the skin is visibly present. On the other hand, as shown in FIG. 6, the present invention dressing 10, because of its microporous structure 12 and the porous adhesive 14, has uniform air permeability 26 throughout the fabric. This overall air permeability contributes to substantial evaporation of any moisture against the skin thus eliminating maceration of the skin. Thus, the present invention is superior over prior art, notwithstanding the fact that the prior art dressing material apparently was more "air permeable" than the dressing material of this invention.

In addition to providing excellent air permeability, micropores, such as described herein, are important because they provide a barrier on the outside surface of the fabric to liquid borne bacteria. It is believed that this is done by stopping the flow of liquid, which may have bacteria in it, through the dressing, by a capillary action force on the micropores which counteracts a driving force caused by a head of liquid. By preventing liquid from penetrating a dressing, a wound will remain isolated from any bacteria or liquid present. Thus, this is another advantage that the present invention has over the prior art.

FIG. 5 illustrates the large size openings 32 that are evident in a visual inspection of the prior art dressing. These large openings 32 allow liquid to freely enter into the dressing. FIGS. 3 and 6 show the present invention, and illustrate that the pores within the present invention are of micro proportion and are not evident by a visual inspection. As explained in the following tests, the micopores of the present invention repell liquid and do not allow it to enter through the dressing itself.

To determine whether a fabric can hold back liquid, it is subjected to two tests—the Mason Jar Test and the Hydrostatic Head Test. The Mason Jar test is conducted according to the Industrial Nonwoven Disposable Association Standard Test, IST 80.7-70(R77), and the Hydrostatic Head Test is conducted according to the American Association of Textile Chemists and Colorists, AATCC-127-1974 and IST 80.0-70(R77). The Mason Jar Test is to determine the time it takes liquid to penetrate the fabric when said fabric is under a head of water of 4.5 inches, and the Hydrostatic Head Test is conducted to determine the amount of water pressure the fabric can withstand before water passes through said fabric.

It should be noted that the microsized fabric of the present invention dressing satisfactorily passed all the aforementioned tests as is evident in Table 1.

TABLE 1

| PROPERTIES OF MICROSIZED FABRIC | | |
| --- | --- | --- |
| PROPERTY | HOSPITAL ACCEPTABLE VALUES | EXAMPLE I |
| Weight per area, gsy | 50–60 | 53.5 |
| Tensile strength, lb | | |
| MD (Machine Direction) | 15* | 40.4 |
| CD (Cross Direction) | 12* | 13.4 |
| Elongation at break, % | | |
| MD | — | 25.6 |
| CD | — | 183.3 |
| Mullen Burst, psi | 30* | 57.8 |
| Tongue Tear, lbs | | |
| MD peak | — | 2.0 |
| Average | 1.5* | 1.5 |
| CD | 1.5* | no tear |
| Energy to tear, inch-lb | — | 8.9 |
| Handle-o-meter, gm force | | |
| MD | — | 85.7 |
| CD | — | 8.1 |
| Overall | 50** | 47 |
| Air Permeability, (Without Adhesive) | | |
| Frazier cuft/sqft/min | 50* | 103.5 |
| Hydrostatic Head, inches of water | 9* | 9.5 |
| Mason Jar Test, min. (5 samples required) | 60* | 60+ |
| Abrasion, cycles to 1st pill | 120+ | |
| Outer Face | 15* | 22 |
| Inner Face | 15* | 26.2 |
| Cytotoxic Test (Living tissue test) | Passed | Passed |

*minimum value
**maximum value

The following is an example of the present embodiment, and is not intended to limit the present invention, except as to the claims.

EXAMPLE 1

A 40.8 (gsy) grams per square yard 100% polyester hydroentangled fabric, such as sold by DuPont Inc., located in Delaware, and identified as P004 was micro-sized in a continuous process by applying, via a knife-over-roll applicator, an ethyl-butyl acrylate-clay froth of the composition as described in U.S. Pat. No. 4,499,139.

The froth applied in this Example was first aerated by an Oakes Foamer, Model No. 4MT2A to a density of approximately 160 grams per liter by rotating the mixing head at 1125 revolutions per minute and pumping at a setting of 180 (approximately 200 grams per minute). The back pressure at the foamer was 55 pounds per square inch of gage. The froth was fed batch-wise in 5-10 minute intervals to the knife-over-roll applicator. The gap between the knife and roll was set at 11 mils. The fabric weighed 40.8 (gsy) grams per square yard before microsizing and 53.5 gsy thereafter.

Figure 2:
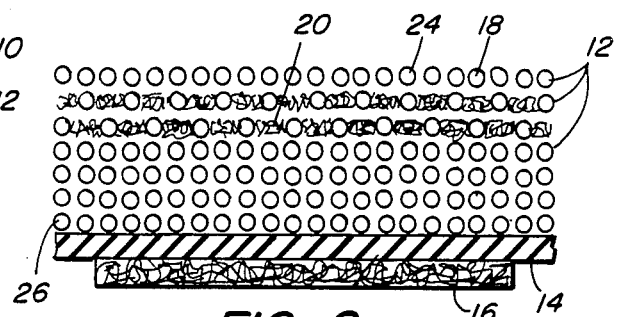
FIG. 2 shows a magnified cross-sectional view of FIG. 1 along A—A.

The process line speed was 10 feet per minute. After applying the froth the microsized web was dried in an air circulating oven with three zones set at 210° F., 225° F., and 250° F., respectively. The sizing penetrating into the fabric, was 60-80 microns of the total 300 micron fabric thickness. The outer surface fibers, 24 as shown in FIGS. 1, 2 and 3 were substantially left uncoated. The average pore size was between 20 and 40 microns, with a few pores at 80 microns.

The fabric was then passed thru a knife-over-roll applicator whereby a porous solvent base synthetic polyacrylate adhesive was applied to the inner surface fibers 26 of the fabric as shown in FIGS. 1, 2 and 3. The adhesive was then cured by passing the composite fabric through an oven.

After curing the adhesive, the fabric was passed through a converting machine manufactured by the Bernal Company of Detroit, Mich., whereby an absorbent nonwoven cotton pad material is applied onto the adhesive 14, and centrally to the micro-porous fabric, as shown in FIG. 4. The adhesive on the fabric thus securing the absorbent nonwoven pad material in place.

The adhesive and pad were then sealed by covering them with a strip of release material to protect them. The release material is designed so as to be removed, before the dressing is placed in contact with the wound.

What is claimed is:

1. A wound dressing comprising at least one ply of an aerated latex microsized porous bacterial barrier fabric, having an adhesive disposed on at least one surface of said fabric, and a nonwoven pad material disposed on said adhesive and secured thereby.

2. The wound dressing of claim 1 wherein said adhesive is a porous pressure sensitive adhesive.

3. The wound dressing of claim 2 wherein said adhesive is a porous polyacrylate.

4. The wound dressing of claim 1 wherein said fabric is an entangled nonwoven fabric.

5. The wound dressing of claim 1 wherein said nonwoven pad material may consist of any natural or synthetic fibers such as from the group consisting of cotton, polyester, rayon, acrylic, polypropylene, nylon or polyethelene or blends thereof.

* * * * *